United States Patent [19]

Jette et al.

[11] Patent Number: 5,075,218

[45] Date of Patent: Dec. 24, 1991

[54] SCREENING FOR ANTIBODIES WHICH BIND CARBOHYDRATE EPITOPES OF TUMOR-ASSOCIATED ANTIGENS, AND USES THEREOF

[75] Inventors: Diane Jette, Edmonton; Anneke Van Heel, Ardrossan; Mavanur Suresh, Edmonton, all of Canada

[73] Assignee: Biomira, Inc., Edmonton, Canada

[21] Appl. No.: 197,882

[22] Filed: May 24, 1988

Related U.S. Application Data

[63] Continuation-in-part of Ser. No. 139,201, Dec. 29, 1987, abandoned.

[51] Int. Cl.$^5$ ............... G01N 33/543; G01N 33/574; G01N 33/577
[52] U.S. Cl. .................... 435/7.23; 436/518; 436/548; 436/809; 436/813; 436/822
[58] Field of Search .......... 435/7, 172.2, 240.27, 435/948, 7.23; 436/548, 813, 822, 809, 518; 530/387, 391, 413, 809; 935/95, 110

[56] References Cited

U.S. PATENT DOCUMENTS

| | | | |
|---|---|---|---|
| 3,654,090 | 4/1972 | Schuurs et al. | 435/7 |
| 4,389,392 | 6/1983 | Adachi | 436/813 |
| 4,471,057 | 9/1984 | Koprowski et al. | 436/813 |
| 4,507,391 | 3/1985 | Pukel et al. | 436/813 |
| 4,579,827 | 4/1986 | Sakamoto et al. | 436/548 |
| 4,607,009 | 8/1986 | Steplewski et al. | 436/528 |
| 4,752,569 | 6/1988 | Terasaki et al. | 436/813 |
| 4,783,420 | 11/1988 | Del Villano, Jr. et al. | 436/548 |
| 4,818,682 | 4/1989 | Linnane | 436/813 |
| 4,837,171 | 6/1989 | Codington | 436/548 |
| 4,851,357 | 7/1989 | Yamashima | 436/528 |
| 4,851,511 | 7/1989 | Hakamori et al. | 436/548 |
| 4,863,854 | 9/1989 | Mattes | 436/548 |
| 4,873,188 | 10/1989 | Hellstrom et al. | 436/813 |
| 4,885,358 | 12/1989 | Kannagi et al. | 530/828 |
| 4,894,442 | 1/1990 | Toyama et al. | 436/548 |

OTHER PUBLICATIONS

Galfre et al., *Meth. Enzymol.*, 73, 21, 1981.

*Primary Examiner*—David Saunders
*Attorney, Agent, or Firm*—Iver P. Cooper

[57] ABSTRACT

Cells which produce antibodies which bind carbohydrate epitopes of glycoproteins are identified by screening with mucinous body fluids in raw, or preferably partially purified, form. Fine differences in antibody specificity may be detected by further screening with mucinous body fluids treated to alter the carbohydrate epitope interest, e.g., removal of sialic acid from a sialosyl Lewis-a epitope. The selected antibodies may be used in immunopurification, immunodiagnosis and immunotherapy.

By this method, antibodies have been found whose binding to carbohydrate epitopes such as sialosyl Lewis-a is relatively insensitive to pH. Such antibodies are of particular value in immunological methods where pH is a consideration.

17 Claims, No Drawings

SCREENING FOR ANTIBODIES WHICH BIND CARBOHYDRATE EPITOPES OF TUMOR-ASSOCIATED ANTIGENS, AND USES THEREOF

This application is a continuation-in-part of Ser. No. 07/139,201, filed Dec. 29, 1987, now abandoned, the full contents of which are incorporated by reference herein. Priority is claimed under 35 U.S.C. 120 and Rule 78(a)(3).

Methods of synthesizing sialosyl Lewis-a and sialosyl Lewis-x oligosaccharides useful in screening of antibodies are described in commonly owned copending applications of Abbas, Diakur and Sugiyama, Ser. No. 07/159,734, filed Feb. 24, 1988 and Ser. No. 07/193,608, filed May 13, 1988.

BACKGROUND OF THE INVENTION

1. Field of the Invention

This invention relates to a method of screening monoclonal antibody-producing clones to identify those producing antibodies which recognize a desired carbohydrate determinant, such as CA 19-9. Such antibodies are useful in immunopurification, immunodiagnosis, and immunotherapy. By this method, we have identified antibodies suitable for immunodetection at physiological pH of antigens bearing the CA19-9 determinant.

2. Information Disclosure Statement

Tumor-associated antigens are antigens which are present in the serum and tissues of cancer patients. Many such antigens are also expressed in embryonic tissues, and, at low levels, in the tissue and serum of healthy individuals. Many of the tumor-associated antigens are glycoproteins, glycolipids, or mucopolysaccarides.

The portion of an antigen to which an antibody binds is called the antigenic determinant, or epitope. An antibody raised against a glycoprotein may recognize a protein epitope, a carbohydrate epitope, or an epitope formed by the junction of the protein and carbohydrate moieties. It is known that the terminal carbohydrate sequence of a glycolipid may also be found on a glycoprotein, thus, a glycolipid and a glycoprotein may bear the same carbohydrate epitope. See Rauvala and Finne, FEBS Lett., 97:1 (1979); McIlhiney, et al., Biochem. J., 227: 155 (1985).

Hakomori, "Monoclonal Antibodies Directed to Cell-Surface Carbohydrates", in *Monoclonal Antibodies and Functional Cell Lines: Progress and Applications* Ch. 4 (1984) discusses the development of various anti-carbohydrate monoclonal antibodies. He notes that there are various difficulties in producing these antibodies. According to Hakomori, carbohydrate moieties in glycoproteins are only weakly immunogenic. While the carbohydrate chains in some glycolipids are said to be strongly immunogenic, others reportedly were weakly immunogenic, or perhaps not immunogenic at all An ideal antibody reagent would always bind all to all antigens of interest, and only to those antigens; in practice, a modest degree of cross-reactivity is tolerated, which varies from one application to the next.

Only about seven monosaccharides have been identified in the oligosaccharides of mammalian glycoproteins and glycosphingolipids. These are sialic acid (acetylneuraminic acid), N-acetyl-D-galactosamine (GalNAc), N-acetyl-D-glucosamine (GlcNAc), D-galactose (Gal), D-mannose (Man), D-glucose (Glu) and L-fucose (Fuc). Glycosphingolipids are composed of a base (e.g., sphingosine), a fatty acid, and carbohydrate. The base is linked to the fatty acid via an amide linkage, and this substructure is called ceramide. The ceramide is glycosidically linked to the carbohydrate. Gangliosides are sialic acid-containing glycosphingolipids. The carbohydrate moieties of GSLs are the immunodominant portion of the molecule. See Yogeeswaran, "Cell Surface Glycolipids and Glycoproteins in Malignant Transformation", 38 *Advances in Cancer Research* 289 (1983).

One of the first tumor-associated glycoproteins to be identified was carcinoembryonic antigen. See Hansen, U.S. Pat. No. 4,180,499. As many as nine to twelve Fab antibody fragments may bind simultaneously to this 180,000 dalton molecule. Egan, et al., Cancer, 40: 458 (1977). The majority of the antigenic sites for which antibodies are available are polypeptide regions, however, antibodies which recognize carbohydrate epitopes of CEA are known. See Nichols, et al., J. Immunol., 135: 1911 (1985). Many anti-CEA antibodies react with binding sites which are dependent on the tertiary structure of the protein. Rogers, Biochim. & Biphys. Acta, 695: 227 (1983).

The carbohydrate structures of several erythrocyte glycoprotein and glycolipid antigens are known to behave as tumor and differentiation markers. See Feizi, et al., Nature, 314: 53 (1985).

One family of red blood cell surface antigens is called the "Lewis group." The Lewis-a determinant has been characterized as a trisaccharide, Beta-Gal(1-3)-[alpha-Fuc(1-4)]-GlcNac. Lewis-a determinants are found as terminal sugar sequences on both glycosphingolipids and on glycoproteins. See Watkins, "Biochemistry and Genetics of the ABO, Lewis, and P Blood Group Systems," in 10 *Adv. Human Genetics* Ch. 1 (1980). Artificial Lewis-a determinant-bearing antigens have been prepared. Lemieux, U.S. Pat. No. 4,137,401. Assays for Lewis-a antigens are known. See Steplewski, U.S. Pat. No. 4,607,009.

Monoclonal antibody 19-9, produced by a hybridoma prepared from spleen cells of a mouse immunized with cells of the human colon carcinoma cell line SW1116, detects a serum antigen which appears associated with gastrointestinal and pancreatic cancers.

The antibody 19-9) has been deposited as ATCC HB 8059. Koprowski, U.S. Pat. No. 4,471,057. The epitope of this antibody is reportedly a carbohydrate with the sugar sequence NeuNAc-alpha(2-3)-Gal-beta(1-3)-[Fuc-alpha(1-4)]-GlcNac-beta-(1-3)-Gal. Magnani, et al., Cancer Research, 43: 5489–92 (1983). It should be noted that this "CA19-9" epitope includes what may be described as a sialylated Lewis-a with an additional galactose unit. For its biosynthesis, see Hansson and Zopf, J. Biol. Chem., 260: 9388 (1985). It is known that the binding of 19-9 to CRC cell line SW1116 is abolished by pretreatment of the cells with neuraminidase. U.S. Pat. No. 4,471,057. In SW1116 extracts, it apparently occurs as a ganglioside (with the structure sialosyl-$Le^a$-beta(1-3)-Gal-beta(1-4)-Glc-betal-Ceramide), but in serum, it is expressed as a mucin.

Mucins are glycoproteins of high molecular weight and high carbohydrate content. They are known to be secreted by the seroviscous tissues found in the mouth, lungs, cervix and intestines. They are believed to provide a protective coating, shielding cells from osmotic and pH gradients and from physical trauma. A typical mucin has a molecular weight in excess of 500,000 daltons and a carbohydrate content of 60–80%. A typical mucin may possess as many as 200 oligosaccharide chains attached to a polypeptide backbone. Tumor-associated oligasaccarides on mucins include CA 19-9 (a.k.a. GICA), DuPan-2, CA 1 and YPAN 1. Neuraminidase, an enzyme that selectively cleaves sialic acid from oligosaccharides, alters the antigenic activity of many of these mucins. Tittenhouse, et al., Laboratory Medicine, 16: 556 (1985).

One problem with natural antibody-producing cells is that is difficult to maintain them indefinitely in culture. In 1975, Kohler and Milstein introduced a procedure for the continued production of monoclonal antibodies using hybrid cells (hybridomas). It entailed the fusion of spleen (antibody-producing) cells from an immunized animal with an immortal myeloma cell line in order to obtain immortalized antibody-producing cells. In order to obtain a monoclonal antibody which would recognize a colorectal cancer-associated antigen, Koprowski immunized a mouse with CRC cells. The hydridomas he eventually produced were screened for their ability to produce antibodies which bound the immunizing cells. (It is also possible to obtain cells lines which continue to produce antibodies by other techniques, such as optimization of culture conditions.)

Herlyn, et al., J. Immunol. Meth., 80: 107-116 (1985) describes a typical screening. Mice were immunized with intact tumor cells of various types, spent medium from tumor cell cultures, membranes of tumor cells, glycolipid extracts of tumor cells, and PEG precipitates from the sera of cancer patients. The hybridomas (12,818 in number) were first screened with the spent medium in which cultured normal and malignant cells had been grown. The more promising hybridomas (95) were then screened with the cells themselves. Finally, 40 clones were screened with cancer patients' sera. One antibody, CO 29.11, was selected for detailed study. Its ability to bind to isolated sialylated Lewis-a glycolipid and to Lewis-a was compared to that of the previously developed 19-9 antibody.

Herrero-Zabaleta, Bull. Cancer, 74: 387-396 (1987) reported the use of immunoprecipitated (with antibody 19-9) components of the fluid of a mucinous ovarian cyst for mouse immunization. Splenocytes from the immunized mouse and myeloma cells were fused to obtain hybridomas. The hybridomas were screened for the ability to produce a pattern of immunoperoxidase staining on paraffin sections of esophageal mucosae which was similar to that generated by 19-9. Only the supernatants of five of the 150 hybridoma wells showed reactivity with this material and only one had a pattern similar to that of 19-9. The antibody (121 SLE) was compared with 19-9 for its ability to react with ovarian mucinous cyst extracts. Both were reactive. In addition, samples of the cyst wall were fixed in ethanol, embedded in paraffin, and cut into sections. The sections were then deparaffinized and incubated with neuraminidase. Both antibodies were tested for their ability to bind to the neuraminidase-treated sections and neither exhibited significant reactivity. This is a very time-consuming procedure. Herrero-Zabaleta did not use neuraminidase-treated mucinous cyst fluids in his study, and the his unpurified cyst fluids were used only for characterization and not for screening.

Kortright, WO 87/01392 proposes improving the binding of a monoclonal antibody to a human carcinoma tumor antigen by removing sialic acid which apparently sterically hindered formation of the immuno-complex. Schauer, TIBS 357 (September 1985) discusses the dual role of sialic acid in both masking and accentuating antigenicity, and sets forth the structures of the natural sialic acids.

A heterogeneous immunoassay is one in which the antigen of interest is bound into an antigen-antibody complex, and this complex is physically separated from the remainder of the sample. There are two basic types of heterogeneous immunoassay. In a sandwich assay, the sample antigen is bound by both an immobilized antibody and a labeled antibody, thus forming a ternary complex. For this to be possible, the antigen must bear at least two epitopes sufficiently far apart to permit the antigen to be simultaneously bound by both antibodies. See David, U.S. Pat. No. 4,376,110. Sandwich assays are, unfortunately, prone to displaying a "high dose hook effect." Cragle, U.S. Pat. No. 4,595,661.

In heterogeneous competitive immunoassays, the sample antigen competes with a known quantity of kit antigen for the binding sites of a kit antibody. Either the kit antigen may be labeled and the kit antibody immobilized, or vice versa. Competitive inhibition assays are generally thought to have the disadvantage of a short dynamic standard curve range as compared with sandwiched assays. Moreover, since only one binding event is required to produce a signal, the assay may be less discriminating.

The commercial assays for CA19-9, marketed by Centocor, Abbott, Commissariat a L'Energie Atomique, Hoffman-LaRoche, Inc., Sorin Biomedica and FujiRebio, are all sandwich assays.

Delvillano, Jr., WO 84/00758 describes a forward sandwich immunoassay for CA 19-9. Delvillano states that with regard to detecting CA19-9 antigen with the 19-9 antibody, the preferred pH was 2.5-6.5, and especially 4.5. Table 4 shows the effect of buffer pH on CA 19-9 detection. It is generally known that pH may alter the binding affinity of an antibody, and it has been suggested that the pH of an incubation may be selected to increase specificity. Mosmann, et al., J. Immunol., 125: 1152 (1980). It is also known that acidic pH may dissociate existing antigen-antibody complexes in serum samples. Thomson, et al., PNAS (USA) 64: 161 (1969).

Koprowski, U.S. Pat. No. 4,471,057 did describe a competitive immunoassay for a "monosialoganglioside" bearing the epitope recognized by antibody 19-9 (ATCC HB 8059). A serum sample was incubated with this antibody, and the mixture was then brought into contact with a surface having attached thereto a monosialoganglioside antigen from a known human CRC cell. The assay was commercially impractical, as it included three overnight incubations, two washes, and an indirect signal system. Significantly, none of the aforementioned commercial assays for CA19-9 are competitive assays.

Adachi, U.S. Pat. No. 4,389,392 describes a method for determining the level of tumor-associated glycoprotein or glycolipid in a sample by incubating the sample with a lectin and measuring the amount of bound or unbound lectin. Pukel, U.S. Pat. No. 4,507,391 discloses an immunoassay for a $G_{D3}$ ganglioside. Similarly, Irie, U.S. Pat. No. 4,557,931 discloses an assay for $G_{M2}$ ganglioside.

No admission is made that any of the foregoing references constitute prior art or pertinent prior art, that the publications accurately reflect the actual experimental work of the authors, or that the dates of publication are exact.

SUMMARY OF THE INVENTION

One of the greatest advantages afforded by monoclonal antibodies is that a pre-defined immunogen is not required in order to produce antibodies of a predefined specificity. Increasingly, the problem of understanding the exact binding specificity of an antibody has become the focus of much study. To conduct these studies a significant quantity of antibody is usually required in a purified state; moreover, pure, well-defined antigen is required but is typically expensive to obtain if available at all. The more detailed the understanding of the specificity of an antibody becomes, the easier it is to use it as a reagent or pharmaceutical agent. Although the best immunization and screening procedure for a particular analyte is likely to be for different classes of antigen, a general method for determining which antibodies are useful to study or in order to identify those of a predefined specificity manifested in different classes and subclasses is useful. For example, IgMs have been classifically been thought of as good agglutinating reagents while IgG's have typically been desired for sandwich assays. Moreover, some subclasses are better suited for "antibody dependent cellular cytotoxicity"—based therapy and some antibodies are more easily purified than others.

Typically, the initial screen of a series of monoclonal antibodies is to determine whether or not it reacts with the immunogen. Thereafter, a great number of different combinations of screening procedures have been employed depending on the specific purpose to which an antibody is required (for example see Weltman U.S. Pat. No. 4,689,311). Thereafter, the method of production, screening, purification must be developed and clinical analysis, and studies related to the exact chemical specificity of the antibodies must be conducted.

It is particularly desirable to have a method for quickly making the decision for production in the case of a search for an anti-carbohydrate antibody. The definition of fine specificity of an anticarbohydrate antibody to various components of the epitope is more important than in other antigens in view of the microheterogeneity of carbohydrate-bearing glycoconjugates (for example, Lewis$^a$, CA 50, and CA19-9 may be found on the same mucin molecule). Therefore, while one would attempt to eliminate cross-reactivity whether an antibody was carbohydrate or not, other classes of molecule do not have as many repeating sequences and related structures.

There is considerable interest in identifying monoclonal antibodies which are specific for particular carbohydrate determinants, particularly those containing a terminal sialic acid. However, the screening of hybridomas to identify those producing the desired antibodies is a laborious and expensive process.

Each of the screening materials previously known to the art has its disadvantages. It is known that there may be antigenic differences between tumor cells grown in vitro and those propagated in the human body. See Freifelder, MOLECULAR BIOLOGY (2d ed. 1987); Freshney, ed., ANIMAL CELLS IN CULTURE: A PRACTICAL APPROACH (1986). Consequently, antibodies which bind well to cultured tumor cells, or to their supernates or membrane sonicates, will not necessarily bind to a tumor product naturally expressed at high levels in a patient's body fluids.

A particular antigen may be fully purified from a selected tumor cell, or a synthetic antigen with the same epitope may be prepared. Purification and synthesis are expensive, and availability of substantial quantities of the purified or synthetic antigen is likely to be a problem.

The patient's serum, in raw or partially purified form, may also be used as a screening material. However, ethical considerations limit the amount of blood which may be withdrawn from an individual, particularly one suffering from a life-threatening disease. Moreover, many clinical tests make use of serum samples, so there is a high demand for this material.

For our purposes, we found that the pathological fluids from the thoracic and peritoneal cavities, which are aspirated in the course of normal treatment of the patient and available in large volumes, very useful. Both of these cavities are lined with membranes which secrete small amounts of serous fluids into the cavities. Thus, peritoneal fluid (ascites) is normally secreted by the peritoneum. Under pathological conditions (inflammation or cancer) large amounts of serous or mucinous fluids can be found in these cavities, secreted either by the inflamed membranes of the cavity or by malignant or benign cells in the cavity.

We have found that the mucinous fluids from the thoracic and peritoneal cavities of cancer patients, or from benign or malignant cysts, make excellent screening and immunizing materials. Often, as a result of the cancer, these fluids are overproduced and accumulate. It is usually clinically desirable that the excess fluids be removed from the body, while the removal of blood is usually undesirable. Upon removal, these mucinous fluids are usually discarded. These fluids do not usually accumulate in a healthy patient. When the accumulation is responsive to cancer, it is reasonable to expect that these fluids may be enriched for tumor-associated substances. The glycoprotein antigens, and especially mucin antigens, are of particular interest.

Surprisingly, the glycoproteins, though of nonserological origin, are of value for the screening of antibodies in serodiagnostic assays. (N.B. We will speak interchangeably of screening antibodies and screening clones; it should be understood that it is not the clones themselves but rather their antibodies which are tested.) Moreover, the mucinous fluids may be taken from a patient who is suffering from a different cancer than the one which is to be diagnosed.

It should be noted that materials suitable for use in the characterization of a selected antibody are not necessarily suitable for use in the screening of hundreds or thousands of antibodies. Screening materials must be available in large quantities at a relatively low cost. They must also be easy to handle.

In a preferred embodiment, these mucinous fluids are partially purified to obtain a high molecular weight (usually greater than 200,000 daltons, and preferably greater than 2,000,000 daltons) fraction. The partially purified fractions will mainly comprise mucins, with perhaps a few other high molecular weight materials such as IgM aggregates and antibody:antigen complexes.

Thus, in one embodiment of our invention, a body fluid, accumulated by the body as a consequence of a cancerous condition, is used as a screening material. Preferably, this fluid is a mucinous fluid such as ascites fluid, pleural effusion, or cystic fluid, and desirably, this fluid is partially purified so that it is enriched for mucins. The purification may be by size, since mucins are of high molecular weight, or by affinity, using a lectin or antibody affinity column.

In the case of screening for antibodies which recognize the sialosyl Lewis-a (SLA) determinant, it is desirable to use both the $F_1$ and $F_2$ fractions described hereafter as screening materials since these may include distinct species of SLA-bearing mucins.

Particular mucinous products may serve as positive or negative "screens", depending on the extent to which their component mucins contain the carbohydrate determinant of interest. The use of a negative screen allows one to refine the selection so as to limit the selection to antibodies which are "specific" for the determinant of interest. It should be noted that the term "specificity" is a relative one. Generally, an antibody whose affinity for an interfering species is not more than 5% of its affinity for the analyte of interest would be considered essentially specific; in certain contexts, a higher level of cross-reactivity could be tolerated.

Besides their use as screening materials, these mucinous fluids or partially purified mucins are also useful as immunizing agents in the preparation of the antibody-producing clones. Preferably, a combination of mucins or mucinous fluids from different patients is employed.

In a preferred embodiment of the invention, the antibodies are screened to determined whether they bind to a particular carbohydrate structure of a selected mucin. The native mucin is used as a positive screen and the mucin in a treated form, wherein its carbohydrate structure is changed, is used as the negative screen.

Preferably, the nature of the modification is the removal of one or more of the component sugars (and especially the terminal sugar) of the carbohydrate determinant of interest by a glycosidase. However, the modification could be the addition of one or more sugars to the terminus of the carbohydrate chain by a glycosyltransferase, or the modification of one or more of the sugars by an epimerase or an isomerase. Moreover, it is not necessary that the modification be made enzymatically, though the use of enzymes is preferred.

In the case of a method of screening for antibodies specific for sialylated Lewis-a determinants, it is preferable that the modification be the removal of sialic acid. This may be effected by any sialidase, but preferably by neuraminidase. The sialidase may be one which removes any sialic acid, or it may be specific for a particular sialic acid variant (such as N-glycolyl or O-acetyl sialic acids, see Schauer, supra) or for a sialic acid linked in a particular manner to other sugars.

While the foregoing example is directed to the identification of antibodies which bind to sialoside epitopes of tumor-associated glycoprotein antigens, the method is of more general applicability. Thus the sensitivity of the binding of anti-carbohydrate antibodies to other sugar modifications may be determined. For example, afucosyl mucins may be produced using alpha-L-fucosidase and agalactosyl mucins may be obtained using alpha- or beta-galactosidase or endo- or exo-galactosidase. These may then be used as negative screens in a manner analogous to the use of the asialomucins described previously. In general, the negative screen is preferably a glycoprotein deficient in one of the constituent sugars of the desired epitope but presenting the remaining sugars of that epitope in the appropriate sequence.

It is also preferable that the antibodies be further screened in a hapten inhibition assay, the hapten being an oligosaccharide or glycolipid bearing the epitope of interest. The antibodies additionally may be screened with products obtained by treating the mucins of interest with, as appropriate, an N-glyconase or O-glyconase, or some other deglycosylating agent. This will strip the carbohydrate from the protein backbone of the mucin. That protein may be used as a negative "screen", while the free carbohydrate may be used as a positive "screen".

One may also use traditional screening materials, such as normal or cancer patients' sera, or purified antigens of a known character, in combination with the novel screening materials of the present invention. Most immunogens from human sources contain varying amounts of human serum albumin (HSA), therefore, a negative screen using HSA is usually appropriate.

Selection is not necessarily an absolute process. If few or no antibodies are found which rigorously meet the selection criteria, the criteria may be relaxed. For example, if a panel of several negative screens are used, one might pass an antibody which binds to only one of the negative screens.

Once antibodies are identified that bind to the desired epitope, these antibodies may be used in screening for further antibodies of interest, based on whether they compete with the candidate antibody for a particular epitope.

Certain apparatus may be used to facilitate the screening process. Essentially, this apparatus comprises a support means to which both the positive screen glycoprotein (bearing the unmodified carbohydrate epitope) and the negative screen glycoprotein (bearing the modified carbohydrate) are attached at distinct, known locations. Typically, it will take the form of a microtiter plate, with the positive screen immobilized in a first series of wells and the negative screen immobilized in a second series of wells.

In another preferred embodiment, the screening is carried out at a physiological pH. Antibodies which bind the tumor-associated antigens at physiological pH are more likely to be suitable for use in vivo, e.g., in immunotherapy and immunoimaging.

It is especially preferable that the antibody be screened for its ability to bind the mucin at a wide range of pH values, both below and above physiological pH. An antibody whose binding is essentially pH-insensitive is more likely to be of value in an enzyme immunoassay for the antigen. Enzyme-substrate reactions are often pH dependent; and assay based on an antibody which is essentially insensitive to pH over the pH range of enzyme activity may be conducted at whatever pH is optimal for the enzyme.

It is contemplated that the antibodies identified by the proposed screening method will be used in immunopurification, immunodiagnosis (including serum or urine diagnosis, histochemical studies, and in vivo immunoimaging), immunotherapy, and other immunological methods.

For the purposes of this application, the term "CA 19-9" is used to refer to one or more tumor-associated antigens bound by antibody 19-9 (secreted by hybridoma HB 8059), and apparently a mucin in body fluid. Like antibody 19-9, our preferred antibodies appear to bind a sialosyl Lewis-a determinant of this mucin. The term anti-(CA 19-9) antibody refers to any antibody which binds this mucin, including Koprowski's 19-9 antibody and our own preferred antibodies, whether or not they are cross-reactive. The Centocor CA19-9 RIA, which employs the 19-9 antibody for the detection of CA 19-9 antigen, is referred to hereinafter as the "conventional assay."

By means of this method, we have identified a series of particularly useful antibodies for the sialylated Lewis-a determinant. The binding of these antibodies to that determinant is relatively insensitive to basic and neutral pH, unlike the anti-CA19-9 antibodies known in the art. In addition, by this method, other anti-sialoside antibodies have been generated which essentially do not bind to sialosyl Lewis-a, such as our B32.2 discussed hereafter. Our preferred anti-CA 19-9 antibody is B25.10.

Preferably, an antibody is selected such that the percentage of antigen bound by the antibody within a pH range of 4-9 is always at least about 66% of the percentage of the antigen bound at the pH within the range of 4-9 at which the binding is maximized. This invention is not limited to the detection of CA19-9.

Competitive immunoassays employing these antibodies appear to be able detect cases of cancer which are overlooked by assays employing the convention 19-9 antibody. This may reflect the existence of CA19-9/bearing mucins which present the CA 19-9 epitope only under basic or neutral conditions. That is, certain mucins may be subject to pH-dependent secondary or tertiary conformation changes. Another possible explanation is that there are CA19-9/bearing mucins whose epitopes are so distributed that they cannot participate in the ternary complexes necessary for the success of the sandwich assay format.

Other advantage of the present invention will be apparent to those in the art after perusal of the specification, claims and drawings presented herewith. The appended claims are hereby incorporated by reference as a further enumeration of the preferred embodiments.

DETAILED DESCRIPTION OF THE INVENTION

Preparing the Antigens

We have found that the body fluids of cancer patients, or fractions thereof contain significant levels of mucins bearing CA 19-9 and other tumor-associated antigenic determinants. These body fluids may be obtained by paracentesis of the abdominal cavity to remove ascites fluid, of the thoracic cavity to remove pleural effusions, or of other mucinous fluid-bearing structures such as ovarian cysts, e.g., cystadenomas.

The following table describes a series of body fluids obtained which has been assayed for their content of various tumor markers.

TABLE I

| PE # | Cancer type | Obtained by | Quantity (ml) | CA 19-9* (U/ml) | CEA** (U/ml) | CA 125 (U/ml) | CA 50 |
|---|---|---|---|---|---|---|---|
| 1 | Ovarian Carc. | p | 750 | 26 | 0.75 | 150,000 | 0 |
| 2 | Ovarian Carc. | p | 750 | 24 | 1.0 | 7,100 | 0 |
| 3 | Ovarian Carc. | p | 2480 | 29,866 | 650 | 600 | 2,225 |
| 4 | Ovarian Carc. | p | 1475 | 44 | 1.5 | 25,600 | 0 |
| 5 | Ovarian Carc. | p | 3185 | 31 | 1.5 | 22,400 | 0 |
| 6 | Ovarian Carc. | t | 8 | 39 | 0 | 4071 | 0 |
| 7 | Ovarian Carc. | p | 36 | 53 | 1.5 | 20,793 | 0 |
| 7a | Ovarian Carc. | p | 500 | 62 | 2.75 | 24,100 | 0 |
| 8 | Gastroesophogeal Carc. | p | 4690 | 39 | 19.25 | 2,200 | 0 |
| 8a-1 | Gastroesophogeal Carc. | p | 5000 | 35 | | 111 | 100 |
| 8a-2 | Gastroesophogeal Carc. | p | 5000 | 51 | 18.5 | 0 | 0 |
| 8a-3 | Gastroesophogeal Carc. | p | 1250 | 38 | | 183 | 0 |
| 8b | Gastroesophogeal Carc. | p | 2000 | 48 | 40 | 447 | 0 |
| 8c | Gastroesophogeal Carc. | p | 3500 | 42 | 10.5 | 669 | 0 |
| 9 | Ovarian Carc. | p | 1700 | 34 | 1.25 | 2,500 | 0 |
| 10 | Mucinous ovarian Cystadenoma | | 685 | 62,000 | 9,000 | 4,000 | 6,125 |
| 10a | 1st daughter cyst | | 17 | 54,000 | 50,000 | 13,551 | 7,750 |
| 10b | 2nd daughter cyst | | 12 | 34,000 | 34,250 | 6,039 | 8,000 |
| 11 | pleural carcinoma | | 540 | 33 | 13.25 | 417 | 0 |
| 12 | Lung mesothelioma | p | 5340 | 25 | 12 | 0 | |
| 12a | Lung mesothelioma | p | 4100 | 16 | | 0 | 0 |
| 12b | Lung mesothelioma | p | 7000 | 14 | 0 | 0 | 0 |
| 12c | Lung mesothelioma | p | 7750 | 12 | 0 | 0 | 0 |
| 13 | Ovarian carc. | p | 5190 | 32 | | 2,400 | 0 |
| 14 | Ovarian anaplastic | p | 2940 | 34 | 2.0 | 5,200 | 0 |
| 15 | Colorectal carc. | p | 600 | 1,818 | 1,006 | 1,899 | 250 |
| 15a | Colorectal carc. | p | 2600 | 3,208 | 1,375 | 1,851 | 300 |
| 15b | Colorectal carc. | p | 2000 | 1,560 | 1,175 | 3,225 | 500 |
| 15c | Colorectal carc. | p | 2500 | 2,138 | 950 | 1,905 | 550 |
| 16 | Colorectal carc. | p | 1190 | 92 | 1,575 | 3,200 | 0 |
| 17 | Unknown Primary | p | 170 | 21,717 | 6500 | 1500 | 3,300 |
| 17a | Unknown Primary | p | 400 | 2,132 | 225 | 0 | 425 |
| 18 | Breast Adenocarcinoma | p | 1100 | 32 | 1000 | 4,100 | 0 |
| 18a | Breast Adenocarcinoma | p | 25 | 0 | 26.5 | 183 | 0 |
| 18b | Breast Adenocarcinoma | p | 27 | 0 | 39.5 | 447 | 0 |
| 18c | Breast Adenocarcinoma | p | 41 | 100 | 36.5 | 405 | 100 |
| 19 | Primary unknown carc. | t | 1,100 | 5,745 | 1500 | 2889 | 475 |
| 19a | Primary unknown carc. | t | 1,000 | 2,598 | 1125 | 1335 | 300 |
| 20 | Renal cell carc. | p | 7,140 | 41 | 0.25 | 2,800 | 0 |
| 21 | ? | | 115 | 31 | 3.75 | 1635 | 100 |
| 22 | Ovarian serous cyst (main) | | 215 | 51 | .75 | 79,500 | 0 |
| 22a | Ovarian cyst (daughter) | | 50 | 63 | 0 | 66,200 | 0 |
| 23 | ? | | 3,400 | 41 | 11 | 159 | 0 |
| 24 | Colorectal Carc. | p | 2,300 | 3,773 | 51,000 | 495 | 250 |
| 24a | Colorectal Carc. | p | 3,000 | 2,192 | 35,750 | 159 | 250 |
| 24b | Colorectal Carc. | p | 2,000 | 2,229 | 26,750 | 0 | 25 |
| 25 | Prostate Carc. | t | 4,500 | 38 | 7 | 1041 | 0 |
| 25a | Prostate Carc. | t | 2,500 | 37 | 11 | 1947 | 0 |

TABLE I-continued

| PE # | Cancer type | Obtained by | Quantity (ml) | CA 19-9* (U/ml) | CEA** (U/ml) | CA 125 (U/ml) | CA 50 |
|---|---|---|---|---|---|---|---|
| 26 | Endometrial Carc. | p | 4,000 | 31 | .5 | 1389 | 0 |
| 26a | Endometrial Carc. | p | 3,400 | 30 | 1.0 | 1929 | 0 |
| 26b | Endometrial Carc. | p | 3,750 | 44 | .87 | 1665 | 0 |
| 27 | Not Diagnosed (pleural) | | 250 | 14 | .87 | 0 | 0 |
| 27a | Not Diagnosed (pleural) | | 500 | 33 | .5 | 0 | 0 |
| 27b | Not Diagnosed (pleural) | | | 24 | .75 | 0 | |
| 28 | Ovarian cyst fluid | | 550 | 431,417 | 500 | 82,300 | 8,000 |
| 29 | Pancreatic carc. | p | 250 | 41 | 1.0 | 1,707 | 0 |
| 30 | Not available | | 600 | 669 | 2,500 | 0 | |
| 31 | Metastatic carcinoma (?) | pf | 200 | 15 | 11 | 5883 | |
| 32 | Benign Ovarian cystadenoma | | 50 | 23 | .25 | 17,973 | |
| 33 | Benign | pf | 10 | 56 | 1.75 | 0 | |
| 34 | Undiagnosed | pf | 400 | 17 | 2.25 | 27 | |
| 35 | Not available | | 800 | 50 | 7.0 | 825 | |
| 36 | | pf | 650 | 59 | .25 | 3,165 | |
| 37 | Ovarian Cyst | pf | 4000 | 600,000 | 700 | 20,000 | |
| 38 | | | 570 | 30 | .5 | 675 | |
| 39 | Ovarian carc. | p | 3,625 | 25 | .5 | 500 | |
| 40 | Breast carc. | | 1,275 | 19 | 150 | 1821 | |
| 40a | Breast carc. | | 1,845 | 18 | 122.5 | 789 | |
| 41 | Ovarian cyst | p | 2,695 | 35 | 1.0 | 7,000 | |
| 41a | Ovarian carc. | | 3,000 | 17 | 1.25 | 6,000 | |
| 41b | Ovarian carc. | | 2,120 | 870 | .87 | 2,031 | |
| 41c | Ovarian carc. | | 550 | 29 | | 1,281 | |
| 42 | Primary unknown carc. | p | 5,595 | 22 | .25 | 1,461 | |
| 43 | Breast | | 195 | 13 | 1.0 | 3,459 | |
| 44 | Colorectal carc. | p | 1,650 | 2,450 | 1.0 | 2,163 | |
| 45 | Ovarian carc. | | 1,100 | 1,800 | 30 | 41,500 | | pf = pleural effusion
p = paracentesis
t = Thoracentesis
*Centocor Units
**Hoffman-LaRoche Units
 Centocor Units
 +Stena Diagnostics Units

Purification of Body Fluids

In order to determine the elution pattern on Sephacryl S 500 of some of these fluids, and to make possible the use of different elution pools to coat microtitre plates for screening, the following procedure was used. The body fluids obtained from patients at a local cancer centre are brought up to 3% phenol for sterilization purposes and then clarified by centrifugation for 15 min. at 15,000 rpm (17,500 g) in the SS34 rotor of a Sorvall Centrifuge. The supernatants are then pumped onto a 5×75 cm. Sephacryl S-500 column equilibrated in 10 mM phosphate and 150 mM NaCl, pH 7.2, containing 1 mg/mL of Na $N_3$. The column is eluted with the same buffer at a flow rate of approximately 180 mL/hour, and monitored at 280 nm. Fractions, 12 mL each, were collected and screened for CA 19-9 activity. The first active peak, which occurs in the void volume, is pooled and labelled $F_1$. The second peak of CA 19-9 activity, included in the column but eluted earlier than the main protein peak (as determined by absorbance at 280 nm) is pooled as $F_2$. Several other body fluids have since been fractionated by the same method and a similar elution pattern was observed.

The $F_1$, $F_2$, or a pool of the two fractions of one or two CA 19-9 positive body fluids are coated on a microtitre plate at about 100 U/well to become the positive control for screening culture supernatants of hybridomas. The $F_1$ of a CA 19-9 negative body fluid is coated on the screening plate at approximately the same dilution as the $F_1$ fraction. Then neuraminidase treated (see below for methodology) CA 19-9 positive $F_1$ (the positive control) is coated on the screening plate. Finally, some of the wells of the microtitre plate are coated with HSA. The plate is then blocked with 1% BSA in PBS for at least ½ hour. Hybridoma supernatants which react with the positive control body fluid and none of the others will have the desired reactivity pattern.

To cleave off the terminal sialic acid groups of the partially purified Sephacryl S 500 mucin fractions, the following procedure is used. 10 mL of PE-$F_1$ are incubated overnight at 37° C. with 1.25 mL of neuraminidase-agarose (1.25 U of neuraminidase activity) while tumbling. It is convenient to use fractions which will contain approximately 3000 U/mL of CA 19-9 activity. The neuraminidase-agarose gel is then spun down, and the supernatant is dialyzed overnight against PBS to remove any free saccharides. Chemical estimation shows the reduced content of sialic acid and at least 98% of the CA 19-9 activity in a binding assay is abolished with the asialo mucin preparation.

Preparation of Anti-(CA 19-9) Antibodies

Immunization: Several immunogens have been used, the best in our hands has been the body fluids of this invention. Partially purified ascites mucins (PE3, PE10, PE17, and PE28) rich in SLA activity isolated from Sephacryl S-500 void volume peak were used at doses of 5,000-20,000 U/immunization. Combinations of partially purified mucins of PE3, PE10, PE17, and PE28 have been adopted in various immunizations exploiting long and short-term protocols. See Table IV.

Fusion: Fusions are done using SP 2/0 cell line and according to published protocols. (G. Gafré and Ceasar Milstein (1981) Methods in Enzymology 73:3).

Screening Strategy: Our screening strategy for new clone identification is based on the following procedure.

Hybridoma supernatants are reacted on plates coated in different rows of microtitre wells with a judicious selection of purified CA 19-9 positive and negative mucins (such as PE1, PE3, PE10, PE17, and PE28). The wells are then blocked with BSA. Then 100 μL of each different hybridoma supernatant is added to each of the different antigen coated wells such that antibody from each of the sample hybridoma antibodies contacts one well of each antigen. The mouse monoclonal antibodies bound are detected by an appropriate dilution of goat anti-mouse immunoglobulin conjugated to HPRO (Tago Immunochemicals) and the color is developed by an appropriate peroxidase substrate and chromogen. PE1 is an CA 19-9 negative mucin while PE3 and 17 are positive mucins. Treatment of PE17 with neuraminidase abolishes the reactivity of the mucin in the conventional assay. Additional CA 19-9 positive body fluids such as PE10-f$_1$ and asialo-PE10-f$_1$ (PE10-f$_1$-NA) may be added to increase the resolution of the screening procedure.

Thus, we have an improved screening procedure which would allow others to produce and select SLA reactive clones. More generally this procedure can be adapted to identify any of the cancer-associated sialosides given the appropriate selection of body fluids and derivatized antigen species generated therefrom. In general, we have used PE1, PE3, PE17, asialoPE17, and then HSA as an additional negative control. These results are displayed in Table II.

TABLE II

| Clone # | PE1 | PE3 | PE17 | HSA | asialoPE17 | Tumour Tissue Reactivity |
|---|---|---|---|---|---|---|
| B4.20 | — | ++ | ++ | — | — | |
| B24.7 | — | + | ++ | — | — | |
| B24.8 | — | + | +++ | — | — | |
| B25.7R1 | — | ++ | ++ | — | — | ½+ |
| B25.7R2 | — | ++ | ++ | — | — | ½ |
| B25.9R5 | — | ++++ | +++ | — | — | 2+ |
| B25.6R3 | — | ++ | +++ | — | — | 3+ |
| B25.10R1 | — | ++ | +++ | — | — | 3+ |
| B25.11R3 | — | + | ++ | — | — | 3+ |
| B25.12R1 | — | ++ | + | — | — | 1+ |
| B25.16R1 | — | ++ | +++ | — | — | cells & mucosa |
| B25.17R4 | — | + | + | — | — | 1 |
| B25.18R1 | — | ++ | ++ | — | — | 0 |
| B25.19R5 | — | ++ | ++ | — | — | 0 |
| B25.21R5 | — | ++ | +++ | — | — | cells & mucosa |
| B25.22R3 | — | + | ++ | — | — | 0 |
| B25.23R1 | — | + | + | — | — | 2 |
| B28.2R1 | — | ++++ | ++++ | — | — | |
| B32.2 | — | + | + | — | — | |
| B32.4 | — | ++ | + | — | — | |
| B32.9 | — | + | + | — | — | |
| B32.3 | — | + | + | — | — | |
| B34.1R7 | — | + | + | — | — | |
| B37.4R1 | — | ++ | + | — | — | |
| B37.23R11 | — | ++ | +++ | — | — | |
| B37.35R1 | — | ++ | + | — | — | |
| B37.43R3 | — | +++ | +++ | — | — | |
| B45.1 | — | +++ | +++ | — | — | |
| B45.2 | — | ++ | ++ | — | — | |
| B45.3 | — | +++ | +++ | — | — | |
| B45.7 | — | ++++ | +++ | — | — | |
| B45.13 | — | ++ | + | — | — | |
| B45.16 | — | ++ | +++ | — | — | |
| B45.18 | — | + | + | — | — | |
| B45.24 | — | +++ | +++ | — | — | |
| B67.2 | — | ++ | +++ | — | — | |
| B67.3 | — | ++ | +++ | — | — | |
| B67.4 | — | ++++ | +++ | — | — | |
| B67.5 | — | ++ | +++ | — | — | |
| B67.6 | — | ++ | +++ | — | — | |
| B67.7 | — | + | +++ | — | — | |
| B67.8 | — | ++ | +++ | — | +++ | |
| B67.9 | — | + | ++ | — | — | |
| B67.10 | — | + | ++ | — | — | |
| B67.11 | — | + | +++ | — | — | |
| B67.12 | — | + | +++ | — | — | |
| B67.13 | — | ++++ | ++++ | — | — | |
| B67.15 | — | ++ | +++ | — | — | |
| B67.16 | — | ++ | +++ | — | — | |
| B67.17 | — | ++ | ++++ | — | — | |
| B67.18 | — | + | +++ | — | — | |
| B67.20 | — | + | + | — | — | |
| B67.21 | — | + | + | — | — | |
| B67.23 | — | ++ | ++++ | — | — | |
| B67.24 | — | ++ | ++++ | — | — | |
| B67.25 | — | ++ | ++++ | — | — | |
| B67.27 | + | ++++ | +++ | — | — | |
| B67.28 | — | ++ | ++++ | — | + | |
| B67.45 | — | ++ | + | — | + | |

In the coding system, B is simply a coding device, the first number indicates the fusion number, the post-decimal number indicates the clone, and the number after the R indicates the reclone number. Typically, we choose clones which are PE3(+),PE17(+),PE1(—

),asialoPE17(−), and HSA(−). Asialo-PE3, PE10, asialoPE10, PE28 and other partially purified body fluids have also been successfully used as part of the screening procedure. The above clones have been recloned and the screening repeated on the reclones. Sometime, as in the case of B28.2, recloning assists in resolving the specificity of the antibody (i.e., in the B28.2 case such that the reactivity with asialoPE17 was recloned out). Selected reclones are expanded and ascites are prepared. Immunoglobins are purified by standard affinity or ion exchange methods.

For each antibody we have utilized further, a preferred method of purification was determined. We have used variations of several systems. These methods may not be optimal and other methods may be used depending upon the character of the antibody.

For example, for purifying IgG from ascites, protein A, immobilized on agarose gel, is used for affinity chromatography. The ascites is loaded onto the column at pH 8.5; the bound IgG is then eluted by means of a stepwise pH gradient, between pH 6.0 and 2.5, depending on the IgG subclass of the antibody (See Ey, et. al., Immunochem. 15:429 (1978)).

In contrast, we have generally purified IgM antibodies on a hydroxyapatite column, followed if necessary by a Bakerbond Abx column on HPLC. The hydroxyapatite column was equilibrated in 10 mM potassium phosphate, pH 6.8. The ascites, clarified by centrifugation was diluted ½ in the 10 mM potassium phosphate buffer and located on the column. The monoclonal was subsequently eluted with 90 mM potassium phosphate, pH 6.8, followed by gradient from 90–500 mM potassium phosphate. The purification was monitored by absorbance at 280 nm, and the peak fractions are tested by agarose gel electrophoresis and ELISA.

If sufficient purity was achieved after the hydroxyapatite column, the partially purified monoclonal was diluted in ½ in 100 mM MES pH 5.6 and loaded on a 5μ Bakerbond Abx HPLC column equilibrated in 25 mM buffer. Elution is achieved by a gradient from 25 mM MES, pH 5.4 to 1M sodium acetate, 20 mM MES pH 7.0 over 60 minutes. After dialysis against PBS, the biological activity and purity of the monoclonal antibody is again verified by an ELISA assay and agarose gel electrophoresis and ELISA assay. Other purification methods may be used, depending on the antibody.

Using this system, we readily identified clones which were satisfactory for the purpose of making assays for (CA 19-9)-like determinants.

Hapten Screening

Clones identified by the above procedure are then typically studied for their hapten inhibition characteristics. Polystyrene tubes were coated with a fraction of PE3 at 50 units per tube, diluted in 300 μl of PBS, overnight at room temperature and additional protein binding sites were blocked with 1% BSA in PBS for one hour at room temperature. Then 50 μL of the sialosyl Lewis$^a$ or Lewis$^a$ hapten diluted in normal pooled serum was added to each tube. 250 μL of the radiolabelled antibody (the specific activity is indicated in Table II). The mixture was incubated overnight at room temperature on the benchtop. Tubes were then washed with 2.0 mL of distilled water and counted in a gamma counter (Packard). Normal pooled sera was used as the calibrator for 100% bound or 0% inhibition and percent inhibition or percentage bound (respectively) was calculated. Clones which were reactive with sialosyl Lewis$^a$ but showed little or no reactivity with Lewis$^a$ were chosen for further study.

TABLE III

| Hapten Inhibition of $^{125}$I Monoclonal Antibody Binding to Cancer Antigen | | | | | |
|---|---|---|---|---|---|
| | | | | % Inhibition (μg/tube) | |
| Monoclonal # | Ab (μg/tube) | Input DPM | % Bound | Sialosyl Lewis$^a$ | Lewis$^a$ |
| B25.19R6 | 0.45 | 54,949 | 41 | 52(10) | 3.5(10) |
| B25.16R1 | 0.60 | 61,226 | 41 | 45(20) | 1(20) |
| B25.10R2 | 0.48 | 32,177 | 23 | 36(40) | 5(40) |
| B25.7R1 | 0.36 | 47,718 | 43 | 51(20) | 2(20) |
| B25.17R41 | 0.78 | 28,467 | 27 | 22(40) | 1(40) |
| B28.2R1 | 1.90 | 50,676 | 40 | 17(40) | 4(40) |

Under similar conditions the Centocor anti-(CA 19-9) antibody binding was inhibited by 50% at 8 μg/tube of sialosyl Lewis$^a$ hapten but not by a Lewis$^a$ haptens even at 50 μg/tube.

At this point, clones which react with sialosyl Lewis$^a$ hapten but not by Lewis$^a$ hapten in competition experiments are chosen. Sialosyl Lewis$^a$ haptens similar to those commercially available (a sialosyl Lewis$^a$ hexasaccharide obtained from human milk by Biocarb, Lund, Sweden) can be used in these experiments with analogous results.

A more elaborate hapten screening experiment yielded similar results. Polystyrene tubes (Sarsted) were coated with a fraction of PE37 at 200 units per tube, diluted in 300 μl of PBS, overnight at room temperature. Then, the additional protein binding sites were blocked with 1% BSA in PBS for one hour at room temperature. 50 μl PBS, 1% BSA with our without $4 \times 10^{-5}$M of the appropriate hapten plus 50 μl PBS, 1% BSA containing 5 ng of $^{125}$I labelled monoclonal antibody were added to these tubes and incubated for 3 hours at room temperature on shaker at 200 rpm. The tubes were then washed twice with double distilled water and counted. The percentage bound was determined by the following formula: % Bound=(CPM Bound with Hapten/CPM Bound in the absence of Hapten)×100.

TABLE IIIA

| | Hapten Inhibitions | | | | | | |
|---|---|---|---|---|---|---|---|
| MAb | SLA | CA 50 | Le$^a$ | X | Y | SLX | NANA-lactose |
| B25.10R3 | 55 | 0 | 0 | 0 | 0 | NA | 0 |
| B32.2R2 | 12 | 0 | 0 | 0 | 0 | 0 | 0 |
| B67.4R12 | 89 | 0 | 0 | 0 | 0 | NA | 0 |
| B67.7R22 | 96 | 0 | 0 | 0 | 0 | 0 | 0 |
| B67.17R12 | 98 | 0 | 6 | 0 | 0 | 0 | 3 |
| HB 8059 | 89 | 0 | 0 | 0 | 0 | NA | 0 |

The critical test of the specificity of the antibodies was determined by utilizing a family of closely related haptens. HP 8059 and most of the antibodies were strongly inhibited by the SLA haptens (synthetic tetrasaccharides or natural hexasaccharides). Neither the asialo hapten (Lewis$^a$) or a afucosyl hapten (CA 50) gave significant inhibition. Moreover, this was true for X, Y, Sialosyl Lewis$^x$ (SLX), and NANA-lactose. B32.2 was the only one which was not significantly inhibited by any of the haptens.

Determination of pH Optimums

DelVillano et. al. claim in the PCT WO 84/00758 that higher signal to noise ratios could be obtained by running an immunoassay for CA 19-9 at an acidic pH. In order to test this supposition, a number of our antibodies were tested by the following method.

Polystyrene tubes were coated with a fraction of PE3 at 50 units per tube, diluted in 30 µl of PBS, overnight at room temperature and additional protein binding sites were blocked with 1% BSA in PBS for one hour at room temperature. Either 2 ng. or 10 ng. of $^{125}$I-labelled monoclonal antibodies HB8059, B25.10, B25.16, B28.2, B67.7, and B67.17, were incubated for two hours at room temperature on a shaker in these tubes in phosphate buffers with different pH's. Table IV shows the results:

TABLE IV pH Sensitivity of a Selection of Anti-Sialosyl Lewis$^a$ Clones

| Antibody | % Bound | | | | | |
|---|---|---|---|---|---|---|
| | pH 4 | pH 5 | pH 6 | pH 7.1 | pH 8.1 | pH 9.1 |
| B25.10 (10 ng/tube) | 61 | 62 | 66 | 64 | 62 | 55 |
| B25.10 (2 ng/tube) | 57 | 61 | 63 | 63 | 61 | 53 |
| B25.16 (10 ng/tube) | 30 | 29 | 28 | 28 | 25 | 20 |
| B25.16 (2 ng/tube) | 30 | 29 | 27 | 27 | 23 | 19 |
| B28.2 (10 ng/tube) | 51 | 48 | 56 | 56 | 48 | 54 |
| B28.2 (2 ng/tube) | 51 | 48 | 55 | 56 | 48 | 56 |
| B67.4 (10 ng/tube) | 65 | 63 | 64 | 62 | 58 | 58 |
| B67.4 (2 ng/tube) | 65 | 61 | 64 | 62 | 59 | 56 |
| B67.7 (10/ng/tube) | 43 | 39 | 40 | 38 | 33 | 29 |
| B67.7 (2 ng/tube) | 43 | 39 | 39 | 37 | 31 | 28 |
| B67.17 (10 ng/tube) | 57 | 58 | 59 | 56 | 44 | 39 |
| B67.17 (2 ng/tube) | 57 | 60 | 60 | 57 | 47 | 37 |
| HB 8059 (10 ng/tube) | 64 | 46 | 33 | 17 | 11 | 8 |
| HB 8059 (2 ng/tube) | 61 | 51 | 36 | 17 | 11 | 9 |

The anti-SLA antibodies of the present invention exhibit comparable binding to CA 19-9 mucin coated tubes over a wide range of pH. This result is in sharp contrast to HB 8059 whose optimal binding is at a pH of about 4. Increasing the pH for this antibody drastically reduces the amount bound as well as the affinity.

Serum Sample Screening

We collect and maintain a cancer serum sample bank cross referenced to patient histories collected in accordance with accepted practice of patient consent and confidentiality. All serum assays herein disclosed have used samples from this bank.

After the hapten specificity was determined on the antibodies of Table III, three different set of serum samples for which CA 19-9 values were available were chosen randomly on the day of experimentation. In Table V, various antibodies selected according to the present screening method were tested for the ability to correctly discriminate normal and cancer sera.

TABLE V

B25.10R2 Clinical Screen

Normal Sera

| Patient # | Conventional RIA (Units/mL) | B25.10R2 (% Bound) |
|---|---|---|
| 287 | 17 | 97.7 |
| 288 | 13 | 95.3 |
| 290 | 10 | 97.9 |
| 291 | ND | 96.6 |
| 292 | 34 | 87.5 |
| 293 | ND | 98.1 |
| 296 | 21 | 88.8 |
| 298 | 8 | 87.8 |
| 299 | 51 | 71.2 |
| 300 | 58 | 79.3 |
| 301 | 61 | 111 |
| 303 | 69 | 121 |

Cancer Sera

| Patient # | CA 19-9 RIA (Units/mL) | B25.10R2 (% Bound) |
|---|---|---|
| 902 | 186 | 40 |
| 938 | 237 | 23.9 |
| 1576 | 77 | 64.1 |
| 1607 | 1285 | 13.3 |
| 1835 | 65 | 67.1 |
| 1839 | 26 | 52.4 |
| 1861 | 21 | 71.9 |
| 1891 | 21 | 81.9 |
| 1971 | 6 | 58.9 |
| 1972 | 12 | 86.1 |
| 1980 | 44 | 73.4 |
| 1884 | 14 | 89.3 |

B25.7R1 and B32.2R1 Clinical Screen

Normal Sera

| Patient # | CA 19-9 (Units/mL) | B25.7R1 % Bound | B25.7R1 Units/mL (Arbitrary) | B32.2R1 % Bound |
|---|---|---|---|---|
| 279 | 13 | 68 | 11 | 57 |
| 297 | 13 | 58 | 24 | 71 |
| 298 | 13 | 62 | 16 | 79 |
| 299 | 8 | 61 | 84 | 61 |
| 300 | 8 | 58 | 41 | 71 |
| 301 | 10 | 61 | 14 | 79 |
| 303 | 10 | 69 | 8 | 83 |
| 1483 | 9 | 69 | 12 | 66 |
| 1486 | 12 | 61 | 16 | 76 |
| 1484 | 12 | 84 | 57 | 80 |

Cancer Sera

| Patient # | CA 19-9 (Units/mL) | B25.7R1 % Bound | B25.7R1 Units/mL (Arbitrary) | B32.2R1 % Bound |
|---|---|---|---|---|
| 250 | 3 | 75 | 13 | 72 |
| 255 | 0 | 73 | 16 | 60 |
| 334 | 10 | 59 | 56 | 60 |
| 336 | 10 | 60 | 25 | 64 |
| 754 | 7786 | 10.8 | 2925 | .13 |
| 731 | 165 | 35 | 8488 | 39 |
| 1607 | 1285 | 6.1 | 2056 | 15 |
| 1839 | 33 | 26 | 159 | 49 |
| 1861 | 21 | 41 | 112 | 51 |
| 1971 | 6 | 51 | 468 | 67 |

Inhibition reactions were performed using polystyrene tubes as coated in the hapten inhibition experiments. Radiolabeled anti-(CA 19-9) antibody in 200 µL of PBS at pH 7.2 in 1% BSA was added to each tube together with 100 µL of sample or standard. The reaction mixture was then incubated for 24 hours on shaker at room temperature shaking at 200 rpm. The tubes were washed twice with 2 mL of distilled water. Bound activity was measured in a gamma counter (Packard).

The sandwich assays performed with polystyrene tubes coated with 1 µg of antibody in PBS overnight at room temperature. The tubes were then blocked with 1% BSA in PBS for two hours at room temperature. 100 µL containing 2 ng. (approximately 50,000 CPM) of radiolabeled antibody and 100 µL of either sample or standard solution is added. The mixture was incubated overnight at room temperature on a shaker, washed twice with 2 mL of distilled water, and counted.

All of the tested antibodies exhibit reduced binding to mucin coated tubes in the presence of cancer sera but not normal serum samples. Those serum samples exhibiting the highest CA 19-9 value as determined by a commercial assay also exert the maximum inhibition of the binding of the antibodies. This is true also for B32.2 which is only weakly inhibited by the SLA hapten which is only weakly inhibited by a study of specificity determinations.

B25.16 and B25.10 were selected for further studies. One-hundred-seventy-four serum samples were chosen randomly from the bank and the assayed by the method expressed in the procedure of the B25.10 assay section. One-hundred-seventy-four samples were tested in a 3 hour simultaneous, solid-phase, competitive radioimmunoassay format using either B25.10 or B25.16 as the tracer antibody. A correlation coefficient of 0.95 was determined indicating the clinical comparability of the two antibodies.

B25.10 Containing Simultaneous, Solid-phase, Competitive Inhibition Radioimmunoassy As one embodiment of this invention, CA 19-9 was measured using a simultaneous, solid-phase competitive inhibition radioimmunoassay utilizing monoclonal antibody synthesized by the hybridoma clone B25.10. Polystyrene tubes coated with CA 19-9 epitope-bearing antigen are incubated with standards (10, 40, 75, 150, and 300 IU/ML) made from PE37 in a human serum matrix with 1 mg/mL sodium azide, control (also in a human serum matrix), or a serum sample together with 125-Iodine-labeled B25.10 monoclonal anti-CA 19-9 antibody. During this incubation CA 19-9 bearing antigens will bind the labeled antibodies thereby preventing the binding of these labeled antibodies to the solid phase.

Unbound material is removed by washing the tubes, and radioactivity is measured in a gamma scintillation counter. From the standard curve derived, the CA 19-9 inhibition units (IU) of the unknowns and the control can be determined.

The B25.10 Simultaneous, Solid-phase, Competitive Inhibition Radioimmunoassy Procedure A. Pipette 25 μl of each calibrator, control or patient serum sample to the bottom of the appropriate tubes. The user should note that it is important, due to small sample size utilized, that the sample be pipetted directly to the bottom of the tube. Failure to do so will adversely affect assay precision. Use a fresh pipette tip for each sample.

B. Pipette 200 μl of the $^{125}$I-labeled B25.10 antibody into each tube. For larger number of samples a repeated pipet is very convenient for this step.

C. Thoroughly mix the contents of the tubes by vigorous shaking or gentle vortexing.

D. Cover all tubes with Parafilm ® or equivalent.

E. Place tubes in a water bath at 37°±2° Centigrade and incubate for three (3) hours±five (5) minutes.

F. Aspirate the tubes and wash two (2) times with 2 mL of distilled water. An Oxford pipetter, Cornwall syringe, or equivalent device is suggested for this step. Ensure complete removal of all liquid after each wash.

G. Measure radioactivity of the tubes in a gamma scintillation counter.

RESULTS

Results were obtained by the following procedure:

A. The standard curve is constructed by plotting the mean $^{125}$I cpm for each standard (Y-axis) against the concentration. The curve is then drawn by a "best fitting curve" method. Gamma counters outfitted with automatic data reduction programs (preferably logit-log) may also be used.

B. The concentration of the control and the patient serum samples are determined from the standard curve.

C. Samples reading over 300 units/mL were diluted and reanalyzed for more accurate results. Dilute the sample 1/10 with the 0 units/mL standard. To calculate the result after dilution multiply by 10.

Analytical Sensitivity

The minimal detectable concentration of CA 19-9 was determined to be 3.0 IU. The minimal detectable concentration is defined as that concentration of CA 19-9 equivalent to 2 SD from the 0 IU/mL standard.

Dilution Linearity

Serum samples containing high levels of CA 19-9 were diluted serially with the kit diluent and reassayed. When expected vs actual results were analyzed by linear regression all showed a correlation coefficient ≧0.990.

Expected Values

1. Normal Sera: CA 19-9 levels in sera from normal individuals (blood bank donors) were determined by this assay. It was determined that 98.6% of these normal sera yielded CA 19-9 levels less than 60 IU/mL. The distribution of the values in these normal sera is shown in Table VI.

TABLE VI

| Distribution of 361 Normal sera | |
|---|---|
| Interval IU/mL | # of Samples in Interval |
| 0–5 | 0 |
| 6–10 | 1 |
| 11–15 | 9 |
| 16–20 | 50 |
| 21–25 | 72 |
| 26–30 | 88 |
| 31–35 | 63 |
| 36–40 | 29 |
| 41–45 | 21 |
| 46–50 | 13 |
| 51–55 | 5 |
| 56–60 | 5 |
| 61–65 | 2 |
| 65–70 | 0 |
| >70 | 3 |

2. Malignant Sera: Sera from 319 patients diagnosed with various cancers were tested in this assay. The results shown in Table VII indicated that the B25.10 detected a high proportion of samples of pancreatic cancer.

TABLE VII

| Distribution of CA 19-9 Values in Serum from Patients with Malignant Disease (% In Category) | | | | |
|---|---|---|---|---|
| | N | 0–60 IU/mL | 60–120 IU/mL | >120 IU/mL |
| Colorectal Cancer | | | | |
| Limited Disease | 25 | 84.0 | 12.0 | 4.0 |

TABLE VII-continued

Distribution of CA 19-9 Values in Serum
from Patients with Malignant Disease
(% In Category)

|  | N | 0–60 IU/mL | 60–120 IU/mL | >120 IU/mL |
|---|---|---|---|---|
| Extensive Disease | 43 | 41.9 | 18.6 | 39.5 |
| Total Gastric Cancer | 68 | 57.4 | 16.2 | 26.4 |
| Limited Disease | 27 | 77.8 | 18.5 | 3.7 |
| Extensive Disease | 13 | 23.1 | 46.2 | 30.8 |
| Total Pancreatic Cancer | 40 | 60.0 | 27.5 | 12.5 |
| Limited Disease | 9 | 22.2 | 55.6 | 22.2 |
| Extensive Disease | 8 | 12.5 | 75.0 | 12.5 |
| Total Breast Cancer | 17 | 17.6 | 64.7 | 17.6 |
| Limited Disease | 70 | 84.0 | 7.1 | 11.4 |
| Extensive Disease | 124 | 67.7 | 19.4 | 12.9 |
| Total | 194 | 72.7 | 15.0 | 12.3 |

Comparisons of CA 19-9 Assay Results

The cut off for the assay was selected by applying traditional mathematical criteria to a group of test results on apparently health blood donor specimens (normal values). Our inhibition unit value ranking at the 99th percentile was taken as the upper limit of these normal values (which was defined as 60 IU). This is identical to the method by which the conventional assay cut off of 37 U/mL was originally determined. Although our assay and the conventional assay employ technologically different units, the method employed to determined the upper limit of normal for the two kits was the same. The only difference then is that the same decision criteria was applied to data derived by using two completely different assays formats.

Clinical Sensitivity and Specificity

Although the conventional assay and our unit values showed good numerical correlation, they are not directly comparable because they are measured in two different assay formats. Nevertheless, one can sort results with respect to categories of above (positive result) or below (negative result) the upper limit of normal. Since identical mathematical criteria were applied in determining the upper limit of normal for both kits the "positive" vs. "negative" results are directly comparable. These results can also be used to compare relative clinical sensitivity and clinical specificity for the two kits.

Using the published conventional assay cut off of 37 U/mL and our 60 IU/mL cut off, Table VIII illustrates the increased clinical sensitivity of the our test, especially with respect to Gastric and Pancreatic cancer. Upon some further analysis, these results can be compared with a third qualitative variable; that is, the physician's judgment on diagnosis during patient follow up. These physician judgments were not based on tumor marker results but by consideration of a number of other clinically accepted decision criteria. These diagnosis are the results of physical examination, x-rays, other visualization methods and categorization of other blood chemistries as above or below the upper limit of normal (positive or negative). Unfortunately, we do not have enough data on pancreatic and gastric cancer patients to test the greater specificity of the assay. Nevertheless, we do have a considerable number of serum samples from a population of colorectal cancer patients who have been followed after primary treatment and subsequently diagnosed by standard criteria to be free of disease (FD), disease stable (DS), disease regressive (DR), or disease progressive (DP).

| | Conventional Assay Using HB 8059/Our Assay Using B25.10 | | | | | | |
|---|---|---|---|---|---|---|---|
|  | Gastric Cancer | Colorectal Cancer - DP | Pancreatic Cancer | Colorectal Cancer - DR | Colorectal Cancer - DS | Total Active Cancer* | Colorectal Cancer - FD |
| +/+ | 10 | 17 | 11 | 3 | 5 | 46 | 1 |
| −/+ | 5 | 3 | 3 | 0 | 1 | 12 | 2 |
| +/− | 0 | 1 | 0 | 2 | 1 | 4 | 8 |
| −/− | 25 | 18 | 3 | 8 | 9 | 63 | 69 |
| Correlation R = | 0.96 | 0.84 | 0.99 | 0.99 | 0.83 | 0.86 |  |
| # of Samples | 40 | 39 | 17 | 13 | 16 | 125 | 80 |

In a comparison of assays using the HB 8059 antibody and our B25.10 antibody, we found both capable of detecting elevated serum levels of CA 19-9 antigen (see Table VIII). Generally there is good correlation for all types of cancer and their subgroups. However, for overall active disease, the B25.10 assay is capable of identifying about 8% more cancer than would be negative in the assay employing HB 8059. On the other hand, only about 3% of active disease patients are detected by HB 8059 that is not detectable in the B25.10 assay.

Affinity Constant Determinations of Anti-CA 19-9 Antibodies on a Solid Phase Coated with Multivalent Mucin Experimental setup Mucin-coated tubes were prepared as above. 100 ul/tube of $^{125}I$ labeled monoclonal antibody at molar concentrations typically ranging for these antibodies from $10^{-8}$ to $10^{-10}$M were added. 50 μl PBS with 1% BSA was used for the assays conducted at pH 7.2. For the assay done at pH 4.5, 0.1M citrate containing 1% BSA was used as the buffer. The antibodies were incubated overnight at room temperature on shaker at 200 rpm. The input was counted and the tubes washed twice with double distilled water.

$K_a$ values were determined by double reciprocal plot of 1/[bound] versus 1/[free].($K_a = -X$ intercept)

TABLE IX

| | $K_a$ Values | |
|---|---|---|
| MAb | pH 7.2 | pH 4.5 |
| B25.10R3 | $1 \times 10^9$ | NA |
| B67.4R12 | $3.1 \times 10^8$ | NA |
| B67.7R22 | $0.6 \times 10^8$ | NA |
| B67.17R12 | $3.8 \times 10^8$ | NA |
| HB 8059 | $1.15 \times 10^8$ | $1 \times 10^9$ |

The affinities (or more correctly avidity) of the various antibodies were determined by experiments measuring their binding to mucin coated tubes. B25.10 exhibited the best properties at pH 7.2 and this measurement was comparable to the pH 4.5 Ka for HB 8059. The latter antibody has a logfold lower affinity at physiological pH.

Hybridoma B$_{25.10}$R3 was deposited on Feb. 3, 1988 with the American Type Culture Collection under the Budapest Treaty and received the designation ATCC HB 9636. The making of this deposit should not be deemed license to make, use, or sell the hybridoma or its antibody.

REFERENCES

1. G. Yogeeswaran (1983) Adv. Cancer Res 38, 289.
2. S. Hakomori and Kannagi (1983) J. Natl. Cancer Inst. (USA) 71, 231
3. J. L. Magnani, B. Nilsson, M. Brockhaus, D. Zopf, Z. Steplewski, H. Koprowski and V. Ginsburg (1982) J. Biol. Chem. 257, 14365.
4. J. L. Magnani, Z. Steplewski, H. Koprowski and V. Ginsburg (1983) Cancer Res. 43, 5489.
5. M. Herlyn, H. F. Sears, Z. Steplewski and H. Koprowski (1982) J. Clin. Immunol. 2, 135.
6. B. C. Del Villano, S. Brennan, P. Brock, C. Bucher, V. Liu, M. McClure, B. Rake, S. Space, B. Westrick, H. Schoemaker and V. R. Zurawski Jr. (1983) Clin. Chem. 29 549.
7. R. E. Ritts, B. C. Del Villano, V. L. W. Go, R. Herberman, T. L. Klug and V. R. Zurawski (1984) Int. J. Cancer 33, 339.
8. M. K. Gupta, R. Arciaga, L. Bocci, R. Tubbs, R. Bukowski and S. D. Deodhar (1985) Cancer 56, 277.
9. W. M. Steinberg, R. Gelfand, K. K. Anderson, J. Glenn, S. H. Kurtzman, W. F. Sindelar and P. P. Toskes (1986) Gastroenterology 90, 343.
10. H. Tomoda and M. Furusawa (1986) Jap. J. Surg. 16, 73.

TABLE X

Some Important Tumor-Associated Sialylated Oligosaccharides

| Trivial Name (Tumor Association) | Structure* | Antibody |
|---|---|---|
| Lacto Series (Type I) | | |
| Sialosyl Lewis$^a$ (2 →3) (Colorectal) | Galβ1 →3GlcNAcβ1 →3Gal1 →4Glc →Cer with 2,3 NeuAcα and 1,4 Fucα branches | 19-9; C50 B25.10 |
| Sialosyl Lewis$^a$ (2 →6) (Colorectal) | Galβ1 →3GlcNAcβ1 →3Gal1 →4Glc →Cer with 2,6 NeuAcα and 1,4 Fucα branches | |
| Di-Sialosyl Lewis$^a$ (Colon, gastric, pancreas, lung) | NeuAcα 2,6 ↓ Galβ1 →3GlcNAcβ1 →3Gal1 →4Glc →Cer with 2,3 NeuAcα and 1,4 Fucα branches | FH7 |
| Sialyl Lacto-neo-tertraosyl ceramide (Colon; Terato) | Galβ1 →3GlcNAcβ1 →3Gal1 →4Glc →Cer with 2,6 NeuAcα branch | |
| Sialyl Lacto-neo-tertraosyl ceramide (Colon; Terato) | Galβ1 →3GlcNAcβ1 →3Gal1 →4Glc →Cer with 2,3 NeuAcα branch | K4 |
| Di-sialyl Lacto-neo-tertraosyl ceramide (Colon) | NeuAcα 2,6 ↓ Galβ1 →3GlcNAcβ1 →3Gal1 →4Glc →Cer with 2,3 NeuAcα branch | FH9 |
| Lacto Series (Type II) | | |

TABLE X-continued

Some Important Tumor-Associated Sialylated Oligosaccharides

| Trivial Name (Tumor Association) | Structure* | Antibody |
|---|---|---|
| Sialosyl Lewis$^x$ (2 →3) (Gastrointestinal) | Gal$\beta$1 →4GlcNAc$\beta$1 →3Gal1 →4Glc →Cer<br>↑2,3  ↑1,3<br>NeuAc$\alpha$  Fuc$\alpha$ | CSLEX1 |
| Sialosyl Lewis$^x$ (2 →6) (Gastrointestinal) | Gal$\beta$1 →4GlcNAc$\beta$1 →3Gal1 →4Glc →Cer<br>↑2,6  ↑1,3<br>NeuAc$\alpha$  Fuc$\alpha$ | |
| Dimeric sialosyl Lewis$^x$ (2 →3) (Gastrointestinal) | Gal$\beta$1 →4GlcNAc$\beta\beta$1 →3Gal$\beta$1 →4GlcNAc$\beta$1 →3Gal1 →4Glc →Cer<br>↑2,3  ↑1,3         ↑1,3<br>NeuAc$\alpha$  Fuc$\alpha$       Fuc$\alpha$ | FH6 |
| Trimeric sialosyl Lewis$^x$ (2 →3) (Gastrointestinal) | Gal$\beta$1 →4GlcNAc$\beta$1 →3Gal$\beta$1 →4GlcNAc$\beta$1 →3Gal1 →4Glc →Cer<br>↑2,3  ↑1,3         ↑1,3<br>NeuAc$\alpha$  Fuc$\alpha$       Fuc$\alpha$ | |
| Ganglio Series | | |
| Fucosyl GM$_1$ (Small-cell lung) | Gal$\beta$1 →3GalNAc$\beta$1 →4Gal$\beta$1 →4Glc$\beta$1 →Cer<br>↑2,3            ↑2,3<br>Fuc$\alpha$          NeuAc$\alpha$ | F12 |
| GM$_2$ | GalNAc$\beta$1 →4Gal$\beta$1 →4Glc$\beta$1 →Cer<br>↑2,3<br>NeuAc$\alpha$ | |
| GM$_3$ | Gal$\beta$1 →4Glc$\beta$1 →Cer<br>↑2,3<br>NeuAc$\alpha$ | |
| GD$_2$ (Melanoma) | GalNAc$\beta$1 →4Gal$\beta$1 →4Glc$\beta$1 →Cer<br>↑2,3<br>NeuAc$\alpha$8 →2 NeuAc$\alpha$ | L55 |
| GD$_3$ (Melanoma) | Gal$\beta$1 →4Glc$\beta$1 →Cer<br>↑2,3<br>NeuAc$\alpha$8 →2 NeuAc$\alpha$ | 4.2; R24 |
| GD$_3$(9-O-Acetyl) (Melanoma) | Gal$\beta$1 →4Glc$\beta$1 →Cer<br>↑2,3<br>NeuAc$\alpha$8 →2 NeuAc$\alpha$(9-O-Acetyl) | D1.1 |

These basic structures can have slight variations such as the seen with 9-O-Acetyl GD$_3$ or N-glycolyl GM$_2$.

TABLE XI

| Fusion Code | Host Strain | Fusion Partner | Fusion Process Booster Interval | Route | Amount | Antigen | Adjuvant |
|---|---|---|---|---|---|---|---|
| B3 | rbf/dn | | 1 | ip | 100 | Slam 99 | CFA |
| | | | 7 | ip | 100 | Slam 99 | CFA |
| | | | 5 | ip | 100 | Slam 99 | PBS |
| | | | 1 | ipiv | 200 | Slam 99 | PBS |
| | | | 1 | ipiv | 200 | Slam 99 | PBS |
| | | fox/ny | 156 | ip | 500 | PE - 3 | PBS |
| B4 | rbf/dn | | 1 | ip | 100 | PE 3 | CFA |
| | | | 9 | ip | 100 | PE 3 | CFA |
| | | | 6 | ip | 800 | PE 3 | SAL |
| | | | 1 | ipiv | 400 | PE 3 | SAL |
| | | fox/ny | 1 | ipiv | 400 | PE 3 | SAL |
| B5 | rbf/dn | | 1 | ip | 100 | PE fl | CFA |
| | | | 7 | ip | 100 | PE 3fl | CFA |
| | | | 6 | ip | 800 | PE 3fl | SAL |
| | | | 1 | ipiv | 400 | PE 3fl | SAL |
| | | fox/ny | 1 | ipiv | 400 | PE 3fl | SAL |
| B6 | rbf/dn | | 1 | ip | 106 | SW 1116 | CFA |
| | | | 33 | ip | 106 | SW 1116 | CFA |
| | | | 31 | ip | 106 | SW 1116 | CFA |
| | | | 28 | ip | 106 | SW 1116 | CFA |
| | | | 39 | ip | 106 | SW 1116 | CFA |
| | | | 44 | ip | 106 | SW 1116 | IFA |
| | | fox/ny | 29 | ip | 106 | SW 1116 | IFA |
| B7 | rbf/dn | | 1 | ip | 500 | PE 10 (pel) | CFA |
| | | | 7 | ip | 500 | PE 10 (pel) | CFA |
| | | | 7 | ip | 800 | PE10fl | PBS |
| | | | 1 | ip | 800 | PE10fl | PBS |
| | | fox/ny | 1 | ipiv | 800 | PE10fl | PBS |
| B8 | rbf/dn | | 1 | ip | 100 | PE10fl | CFA |
| | | | 28 | ip | 100 | PE10fl | CFA |
| | | SP2/0 | 34 | ip | 100 | PE10fl | CFA |
| B13 | rbf/dn | SP2/0 | | ip | 108 | Le-a RBC's | PBS |
| B14 | rbf/dn | | 1 | ip | 100 | Pe-3(raw) | CFA |
| | | | 21 | ip | 100 | Pe-3 | CFA |
| | | | 29 | ip | 100 | Pe-3fl | IFA |
| | | | 34 | ip | 100 | Pe-10fl | IFA |
| | | SP2/0 | 45 | ip | 100 | Pe-17fl | IFA |
| B15 | rbf/dn | | 1 | ip: 100 | Pe-3(raw) | CFA | |
| | | | 22 | ip | 100 | Pe-3 | CFA |
| | | | 29 | ip | 100 | Pe-3fl | CFA |
| | | | 34 | ip | 100 | Pe-17fl | CFA |
| | | | 42 | ip | 100 | Pe-10fl | CFA |
| | | SP2/0 | 14 | ip | 100 | Pe-27fl | CFA |
| B16 | rbf/dn | | 1 | ip | 20 | Pe-3(raw) | CFA |
| | | | 22 | ip | 20 | Pe-3 | CFA |
| | | | 29 | ip | 20 | Pe-3fl | IFA |
| | | | 34 | ip | 20 | Pe-10fl | IFA |
| | | | 42 | ip | 20 | Pe-17fl | IFA |
| | | SP2/0 | 16 | ip | 20 | Pe-10fl | IFA |
| B17 | rbf/dn | | 1 | ip | 500 | Pe-10)pel) | CFA |
| | | | 29 | ip | 100 | Pe-10fl | CFA |
| | | | 20 | ip | 100 | Pe-10fl | IFA |
| | | | 35 | ip | 100 | Pe-10fl | IFA |
| | | SP2/0 | 31 | ip | 300 | 3.10.17fl | IFA |
| B18 | rbf/dn | | 1 | ip | 20 | Pe-3(raw) | CFA |
| | | | 22 | ip | 20 | Pe-3 | CFA |
| | | | 29 | ip | 20 | Pe-3fl | IFA |
| | | | 34 | ip | 20 | Pe-17fl | IFA |
| | | | 42 | ip | 20 | Pe-10fl | IFA |
| | | SP2/0 | 24 | ip | 1000 | serum #1606 | IFA |
| B19 | rbf/dn | | 1 | ip | 5 | Pe-10(pel) | CFA |
| | | | 29 | ip | 100 | Pe-10fl | CFA |
| | | | 20 | ip | 100 | Pe-10fl | IFA |
| | | | 42 | ip | 100 | Pe-10fl | IFA |
| | | | 29 | ip | 500 | Pe-3fl | IFA |
| | | SP2/0 | 1 | iv | 1000 | Pe-17fl | PBS |
| B20 | rbf/dn | | 1 | ip | 100 | PE 3fl | CFA |
| | | | 36 | ip | 800 | PE 3fl | PBS |
| | | | 1 | ipiv | 400 | PE 3fl | PBS |
| | | | 1 | ipiv | 400 | PE 3fl | PBS |
| | | | 118 | ip | 400 | PE 3fl | PBS |
| | | SP2/0 | 0 | iv | 2107 | B4 Spleen | MED |
| B25 | Balb/c | | 1 | ip | 2500 | PE 3fl | CFA |
| | | | 15 | ip | 2500 | PE 3fl | CFA |
| | | | 6 | ip | 104 | PE 3fl | PBS |
| | | | 0 | ip | 7250 | PE 17fl | PBS |
| | | | 2 | ip | 104 | PE 3fl | PBS |
| | | | 0 | iv | 7250 | PE 17fl | PBS |
| | | | 1 | ip | 104 | PE 3fl | PBS |

TABLE XI-continued

| Fusion Code | Host Strain | Fusion Process ||||||
|---|---|---|---|---|---|---|---|
| | | Fusion Partner | Booster Interval | Route | Amount | Antigen | Adjuvant |
| | | SP2/0 | 0 | iv | 7250 | PE 17fl | PBS |
| B26 | rbf/dn | | 1 | ip | 100 | PE 17fl | CFA |
| | | | 41 | ip | 100 | PE 17fl | CFA |
| | | | 29 | ip | 500 | PE 3fl | IFA |
| | | | 41 | ip | 2500 | PE 17fl | IFA |
| | | SP2/0 | 7 | ip | 5000 | PE 28/50 | IFA |
| B28 | Balb/c | | 1 | ip | 2500 | PE 3fl | CFA |
| | | | 8 | ip | 2500 | PE 3fl | CFA |
| | | | 6 | ip | 10000/7500 | PE 3fl/PE 17fl | PBS |
| | | | 2 | ipiv | 10000/7500 | PE 3fl/PE 17fl | PBS |
| | | | 1 | ipiv | 10000/7500 | PE 3fl/PE 17fl | PBS |
| | | SP2/0 | 26 | ip | 2000 | PE 28/50 | IFA |
| B29 | rbf/dn | | 1 | ip | 100 | PE 17fl | CFA |
| | | | 41 | ip | 100 | PE 17fl | CFA |
| | | | 29 | ip | 500 | PE 3fl | IFA |
| | | | 41 | ipiv | 2500 | PE 17fl | IFA |
| | | SP2/0 | 14 | ipiv | 2500 | PE 28/50 | IFA |
| B30 | CAF1 | | 1 | ip | 5000 | PE 17fl | CFA |
| | | | 29 | ip | 5000 | PE 17fl | CFA |
| | | SP2/0 | 39 | ip | 45000 | PE 3fl | SAL |
| B32 | CAF1 | | 1 | ip | 5000 | PE 3fl | CFA |
| | | | 29 | ip | 5000 | PE 3fl | CFA |
| | | SP2/0 | 45 | iv | 8750 | PE 10fl | PBS |
| B33 | CAF1 | | 1 | ip | 5000 | PE 3fl | CFA |
| | | | 29 | ip | 5000 | PE 3fl | CFA |
| | | SP2/0 | 49 | iv | 2000/1300 | PE 17fl/PE 28 | PBS |
| B34 | rbf/dn | | 1 | ip | .5 ml | PE 10 (pel) | CFA |
| | | | 29 | ip | 100 | PE 10fl | CFA |
| | | | 20 | ip | 100 | PE 10fl | IFA |
| | | | 42 | ip | 100 | PE17fl | IFA |
| | | | 29 | ip | 500 | PE 3fl | IFA |
| | | SP2/0 | 100 | iv | 8400 | PE 28/50 | PBS |
| B35 | rbf/dn | | 1 | s.c | 100 | PE 17fl | CFA |
| | | | 29 | ip | 50 μg | PE 17fl | IFA |
| | | | 38 | ip | 2500 | PE 17fl | IFA |
| | | | 20 | ip | 5000 | PE 28/50 | IFA |
| | | SP2/0 | 32 | iv | 8750 | PE 10fl | PBS |
| B37 | rbf/dn | | 1 | s.c | 100 | PE 17fl | CFA |
| | | | 29 | ip | 50 μg | PE 17fl | IFA |
| | | | 38 | ip | 2500 | PE 17fl | IFA |
| | | | 20 | ip | 5000 | PE 28/50 | IFA |
| | | SP2/0 | 39 | iv | 8000 | PE 10fl | SAL |
| B38 | rbf/dn | | 1 | s.c | 100 | PE 17fl | CFA |
| | | | 41 | ip | 100 | PE 17fl | CFA |
| | | | 29 | ip | 500 | PE 3fl | IFA |
| | | | 41 | ip | 2500 | PE 17fl | IFA |
| | | | 37 | ip | 5000 | PE 28/50 | IFA |
| | | fox/ny | 60 | iv | 8250 | PE 37fl | PBS |
| B40 | rbf/dn | | 1 | ip | 100 | PE 17fl | CFA |
| | | | 41 | ip | 100 | PE 17fl | CFA |
| | | | 29 | ip | 500 | PE 3fl | IFA |
| | | | 41 | ip | 2500 | PE 17fl | IFA |
| | | | 37 | ip | 5000 | PE 28/50 | IFA |
| | | | 52 | iv | 3000 | PE 37fl/40 | PBS |
| | | SP2/0 | 16 | iv | 3000 | PE 37fl/40 | PBS |
| B45 | Balb/c | | 1 | ip | 5000 | PE 28/60 | CFA |
| | | | 28 | ip | 5000 | PE 28/60 | CFA |
| | | | 44 | ip | 3333 | PE 3fl | WGA |
| | | SP2/0 | 16 | ip | 8333 | PE 37fl | WGA |
| B67 | CAF1 | | 1 | sc | 5000 | PE37fl | CFA |
| | | | 31 | ip | 5000 | PE28f2 | IFA |
| | | | 21 | ip | 5000 | PE37fl | IFA |
| | | | 15 | ip | 5000 | PE37fl | PBS |
| | | | 19 | ip | 5000 | PE37fl | PBS |
| | | | 18 | ip | 5000 | PE37fl | PBS |
| | | SP2/0 | 39 | iv | 10000 | PE 28 AP | PBS |
| B74 | CAF1 | | 1 | sc | 5000 | PE 37fl | CFA |
| | | | 31 | ip | 5000 | PE 28f2 | IFA |
| | | | 21 | ip | 5000 | PE 37fl | IFA |
| | | | 15 | ip | 5000 | PE 37fl | PBS |
| | | | 19 | ip | 5000 | PE 37fl | PBS |
| | | | 18 | ip | 5000 | PE 37fl | PBS |
| | | | 39 | ip | 5000 | PE 37fl | PBS |
| | | | 14 | ip | 5000 | PE 37fl | PBS |
| | | | 31 | ip | 5000 | PE 37fl | PBS |
| | | | 14 | ip | 10000 | PE 37fl | PBS |
| | | SP2/0 | 10 | sc | 10000 | PE 37fl | PBS |

We claim:

1. A method of screening a plurality of antibody producing clones to identify clones producing antibodies which specifically bind a particular carbohydrate structure which comprises incubating the antibody produced by each such clone with (a) a positive screening reagent consisting essentially of a mucin-enriched fraction of a mucinous cystic, peritoneal or thoracic body fluid, said fraction comprising a plurality of mucin components, at lest one component mucin of said fraction presenting said carbohydrate structure, and with (b) a negative screening reagent consisting essentially of a composition prepared by treating said mucin-enriched fraction of a mucinous body fluid with an enzyme which modifies said carbohydrate structure, and selecting clones whose antibodies bind more strongly to said positive screening reagent than to said negative screening reagent.

2. The method of claim 1 in which the mucin-enriched fraction is obtained by carbohydrate affinity chromatography.

3. The method of claim 1 in which the mucin-enriched fraction consists essentially of molecules having a molecular weight of no less than 200,000 daltons.

4. The method of claim 3 in which the fractions comprise of molecules having a molecular weight of no less than 2,000,000 daltons.

5. The method of claim 1 in which the enzyme is a glycosidase which selectively removes a predetermined sugar of mucins of said mucin-enriched fraction.

6. The method of claim 5 in which the glycosidase is a sialidase and the removed sugar is sialic acid or a derivative thereof.

7. The method of claim 5 in which fucose is removed.

8. The method of claim 5 in which galactose is removed.

9. The method of claim 1 in which the enzyme is a glycostransferase which selectively adds a predetermined sugar to mucins of said mucin-enriched fraction.

10. The method of claim 1 in which the enzyme is an isomerase which selectively modifies a predetermined sugar of mucins of said mucin-enriched fraction.

11. The method of claim 1, further comprising selecting clones whose antibodies essentially do not bind to a third screening reagent consisting essentially of a glycoprotein known not to bear said carbohydrate structure.

12. The method of claim 1, further comprising identifying clones whose antibodies are competitively inhibited from binding to said positive screening reagent by a hapten bearing a carbohydrate determinant possessed by said carbohydrate structure of a mucin of said positive screening reagent, but absent from said negative screening reagent as a result of the enzymatic modification.

13. The method of claim 1 in which said mucin-enriched fraction is derived from mucinous body fluids from a plurality of patients who produce such fluids.

14. The method of claim 1 wherein the antibody is incubated with a screening device comprising said positive and negative reagents and a support means to which the positive and negative reagents are attached at distinct and known locations.

15. The method of claim 14, wherein a first and second series of depressions are formed in the support means, and the positive reagent is attached to the support means within the first series of depressions, and the negative reagent is attached to the support means within the second series of depressions, said depressions being provided to receive said antibodies.

16. The method of claim 1 in which only those clones shown to produce antibodies which bind more strongly to the positive screening reagent than the negative screening reagent are subcloned and expanded.

17. A process for producing an antibody which specifically binds a particular carbohydrate structure which comprises identifying a clone producing such an antibody by the screening method of claim 1 and cultivating said clone or antibody-producing derivative thereof under conditions suitable for antibody production.

* * * * *

UNITED STATES PATENT AND TRADEMARK OFFICE
CERTIFICATE OF CORRECTION

PATENT NO. : 5,075,218
DATED : December 24, 1991
INVENTOR(S) : JETTE et al.

It is certified that error appears in the above-identified patent and that said Letters Patent is hereby corrected as shown below:

Column 17, line 17   After "B28.2,", insert
                     -- B67.4, --

Columns 21 and 22, after line 16, above the table, insert the heading -- TABLE VIII --

Column 23, line 6    Delete "B25.10R3", insert
                     therefor -- B25.10R3 --

Signed and Sealed this

Tenth Day of August, 1993

Attest:

MICHAEL K. KIRK

Attesting Officer          Acting Commissioner of Patents and Trademarks